United States Patent [19]

Hesse et al.

[11] Patent Number: 4,670,190

[45] Date of Patent: Jun. 2, 1987

[54] 1-α-HYDROXY VITAMIN D COMPOUNDS AND PROCESS FOR PREPARING SAME

[76] Inventors: Robert H. Hesse, 49 Amherst St., Cambridge, Mass. 02142; Ezzio Rizzardo, 14, Hopegood Place, Garran, ACT 2605, Australia; Derek H. R. Barton, 47 Onslow Square, London S.W. 7, England

[21] Appl. No.: 657,270

[22] Filed: Oct. 3, 1984

Related U.S. Application Data

[63] Continuation of Ser. No. 571,738, Jan. 18, 1984, abandoned, which is a continuation of Ser. No. 348,778, Feb. 16, 1982, abandoned, which is a continuation of Ser. No. 210,330, Nov. 25, 1980, abandoned, which is a continuation of Ser. No. 125,108, Feb. 27, 1980, abandoned, which is a continuation of Ser. No. 922,659, Jul. 7, 1978, abandoned, which is a continuation of Ser. No. 817,825, Jul. 21, 1977, abandoned, which is a continuation of Ser. No. 538,259, Jan. 3, 1975, abandoned, which is a continuation-in-part of Ser. No. 362,339, May 21, 1973, Pat. No. 3,901,928, which is a continuation-in-part of Ser. No. 322,462, Jan. 10, 1973, abandoned.

[51] Int. Cl.[4] ............................................... C07J 9/00

[52] U.S. Cl. .................................. 260/397.2; 514/167; 540/78

[58] Field of Search ..................................... 260/397.2

[56] References Cited

U.S. PATENT DOCUMENTS 3,741,996  6/1973  De Luca et al. ................. 260/397.2

OTHER PUBLICATIONS

Barton et al., "Journal Amer. Chem. Soc.", vol. 95 (1973) p. 2748.

Primary Examiner—Elbert L. Roberts
Attorney, Agent, or Firm—Bacon & Thomas

[57] ABSTRACT

The invention provides novel 1α-hydroxy vitamin D compounds and a method for their preparation from 1α-hydroxy-25-hydrogen cholesta-5,7-dienes by irradiation and isomerization techniques. The invention also includes the said 1α-hydroxy-25-hydrogen-cholesta-5,7-dienes and the corresponding cholest-5-enes.

The new compounds may be obtained in a crystalline form substantially free from isomeric or other impurities arising from manufacture.

2 Claims, No Drawings

1-α-HYDROXY VITAMIN D COMPOUNDS AND PROCESS FOR PREPARING SAME

This application is a continuation of application Ser. No. 571,738, filed Jan. 18, 1984, which is a continuation of Ser. No. 348,778, filed Feb. 16, 1982, which is a continuation of Ser. No. 210,330, filed Nov. 25, 1980, which is a continuation of Ser. No. 125,108, filed Feb. 27, 1980, which is a continuation of Ser. No. 922,659, filed July 7, 1978, which is a continuation of Ser. No. 817,825, filed July 21, 1977, which is a continuation of Ser. No. 538,259, filed Jan. 3, 1975, all abandoned, which is a continuation-in-part of Ser. No. 362,339, filed May 21, 1973, now U.S. Pat. No. 3,901,928, which is a continuation-in-part of Ser. No. 322,462, filed Jan. 10, 1973, abandoned.

This invention relates to 1α-hydroxy-25-hydrogen-vitamin D compounds and 1α,3β-dihydroxy cholest-5-enes and cholesta-5,7-dienes, which are important intermediates in their synthesis.

1α-hydroxy vitamin D derivatives having also a 25-hydroxy group are known to possess advantageous biochemical properties which render them of considerable use in therapy. Thus they are both quicker acting and more quickly eliminated from the system than the corresponding 1α-unsubstituted compounds, and as a result are less likely to induce vitamin toxicity than the conventional vitamin D compounds, which are only slowly eliminated from the system. Furthermore, the hydroxylated derivatives are often effective in alleviating symptoms of apparent vitamin D deficiency which do not respond to treatment with the conventional vitamins.

Such 1α-hydroxy vitamin D derivatives may be prepared by analogous techniques to those employed in the synthesis of the corresponding 1α-unsubstituted derivatives, particularly by photochemical degradation of 1α,3β-dihydroxy steroid-5,7-dienes of the cholestane series using UV irradiation.

Useful precursors for the 1α,3β-dihydroxy steroid-5,7-diene starting materials are the corresponding steroid-5-enes, since these may be readily converted to the 5,7-diene by, for example, bromination at the 7-position followed by dehydrobromination. The synthesis of such 1α,3β-dihydroxy steroid-5-enes, however, gives rise to a number of problems since it is generally necessary to introduce the 1α-hydroxyl group by a Michael-type addition to a Δ$^{1,2}$-3-ketosteroid. Thus subsequent formation of the desired 5,6-double bond is made difficult by the tendency of the 1α-hydroxyl group, which is situated β to a carbonyl group, to eliminate, while it is also difficult to reduce the 3-keto group to a 3β-hydroxy group with high stereospecificity using known techniques.

A synthetic route to 1α-hydroxycholesterol is described by Pelc and Kodicek (J. Chem. Soc., 1970 (C), 1624), this involving epoxidation of 6β-hydroxy-5α-cholest-1-en-3-one, reduction of the product to the 1,2-epoxy-3β-hydroxy derivative using sodium borohydride, elimination of the 6β-hydroxyl group to give the corresponding Δ$^{5,6}$-steroid, and reduction with lithium aluminium hydride to give the 1α,3β-diol. The product obtained by this method does not, however, exhibit the expected physical properties; thus the optical rotation is given as $[\alpha]_D = 0 \pm 1°$ (in MeOH), whereas Δ$^{5,6}$-sterols are normally characterised by a fairly substantial negative specific rotation, typically about $-30°$. Also, the found atomic analysis figures of C, 76.2; H 11.1% do not agree well with those calculated for $C_{27}H_{46}O_2 \cdot 0.5\ H_2O$ (C 78.8; H 11.5%) and the structure of this product must therefore be regarded as open to doubt. One possible source of error is the borohydride reduction of the 3-keto group, which may well give a significant amount of the 3α-ol in addition to the desired 3β-ol.

A somewhat similar synthetic route to the steroid precursor for 1α,25-dihydroxycholecalciferol has been described by DeLuca and co-workers (Tetrahedron Letters 40, 4147, 1972). These workers epoxidised the appropriate steroid-1-en-3-one-6-(ethylene ketal) and then reduced the product with lithium aluminium hydride to yield a mixture from which only the 1α,3α-diol could be separated. Several additional process steps, involving oxidation to the 3-one and reduction with sodium borohydride, were therefore necessary to yield the 1α,3β-diol before removal of the 6-ketal grouping, reduction to the 6-hydroxyl compound and dehydration to give the Δ$^{5,6}$-steroid could be effected, making the overall route somewhat cumbersome.

There is thus a need for a simpler method of preparing 1α,3β-dihydroxy steroid-5-enes which permits ready control of the stereochemistry of the products, particularly at the 3-position, and it is an object of this invention to provide such a method.

Other objects, advantages and aspects of this invention will become apparent from the detailed description and claims which follow.

The essence of the invention is the discovery that 1α-hydroxy- and 1α,2α-epoxy-steroid-4,6-dien-3-ones and corresponding 6-substituted steroid-4-en-3-ones where the 6-substituent is a reductively eliminatable atom or group may be reduced directly to the corresponding 1α,3β-dihydroxy steroid-5-ene by reaction with an alkali metal/liquid ammonia or alkali metal/liquid amine reducing agent in the presence of a proton source. Under these conditions the highly oxidised starting materials undergo sequential reduction to the desired product with substantially no isomerisation of double bonds or elimination of substituents situated β to the 3-position carbonyl group.

The process is particularly applicable to the preparation of 1α-hydroxy steroids of the cholestane series which are precursors for 1α-hydroxylated vitamin D derivatives.

The term "cholestane series" as used herein includes steroids having in the 17-position the $C_8$ chain characteristic of cholestanes, as well as analogous compounds in which this chain is unsaturated or carries one or more hydroxy or methyl groups, these being the 17-side chains found in the D vitamins. Suitable ketone starting materials for the preparation of such 1α-hydroxy steroids of the cholestane series may be represented by the formula

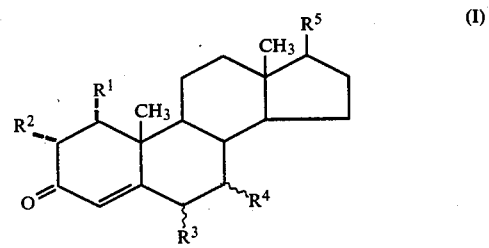

where $R^1$ represents a hydroxy group and $R^2$ represents a hydrogen atom or $R^1$ and $R^2$ together form an epoxide group

$R^3$ represents a reductively eliminatable atom or group and $R^4$ represents a hydrogen atom or $R^3$ and $R^4$ together form a carbon-carbon double bond, and $R^5$ represents a group

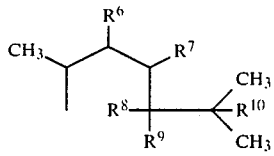

where $R^6$ and $R^7$ each represent hydrogen atoms or hydroxyl groups or together form a carbon-carbon double bond or epoxy group, $R^8$ and $R^{10}$, which may be the same or different, each represent a hydrogen atom or a hydroxyl group, and $R^9$ represents a hydrogen atom or a methyl or ethyl group.

Reduction of a compound of formula I in accordance with the process of the invention leads to formation of a $1\alpha,3\beta$-diol which may be represented by the formula

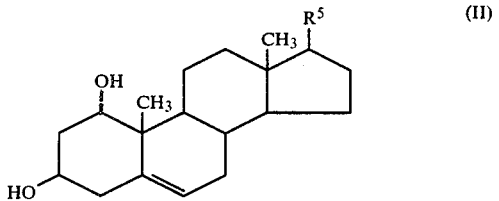

where $R^5$ is as defined for formula I.

$1\alpha,3\beta$-Dihydroxy-25-hydrogen-cholest-5-enes and their hydroxyl-protected derivatives are new compounds.

Reductively eliminatable substituents which may be present at the 6-position of the starting material, e.g. as the group $R^3$ in formula I, include, for example, halogen atoms such as fluorine, chlorine or bromine atoms and hydrocarbon sulphonate groups e.g. aromatic hydrocarbon sulphonate groups such as p-tosylate or aliphatic hydrocarbon sulphonate groups such as mesylate groups.

Alkali metals which may be used in the reducing agent include lithium, calcium, sodium and potassium, lithium being the preferred metal. Liquid amines which may be used include, for example, primary, secondary and tertiary alkylamines, e.g. primary lower alkylamines such as methylamine or ethylamine, di(lower alkyl)amines such as dimethylamine or diethylamine, and tri(lower alkyl)amines such as triethylamine; diamines, e.g. lower alkene diamines such as ethylenediamine or propylenediamine; and saturated heterocyclic amines e.g. piperidine or piperazine. A particularly preferred reducing agent is lithium and liquid ammonia.

Proton sources which may be used in the reaction include ammonium and amine salts, e.g. salts derived from mineral acids, such as the halides, e.g. fluoride or chloride, nitrate or sulphate. Alcohols, e.g. lower alkanols such as methanol or ethanol, may also serve as the proton source.

The reduction is conveniently carried out in a solvent, preferably an inert organic solvent such as a cyclic ether, e.g. tetrahydrofuran or dioxan or a hydrocarbon solvent such as hexane. It may be advantageous to exclude moisture and/or oxygen from the reaction system. Where a solvent is used the reduction is conveniently carried out at a temperature between the freezing point of the solvent system and 100° C., advantageously in the cold.

Various modes of addition may be employed to bring together the reactants. Thus, for example, a solution of the steroid may be added in one or more portions to a solution of the alkali metal in liquid ammonia or a liquid amine, with subsequent addition in one or more portions of the proton source. Alternatively, improved yields and/or greater ease of isolation of the reduced steroid may be achieved if a proton source such as solid ammonium chloride is initially added to a solution of the steroid starting material and the alkali metal/liquid ammonia or liquid amine reducing agent is then added in portions.

It is generally preferred to protect $1\alpha$-hydroxy groups in the steroid starting materials, e.g. with a cleavable protecting group, since reduction of a steroid having a free $1\alpha$-hydroxyl group may result in formation of a $\Delta^{6,7}$-steroid as a result of internal proton transfer. Suitable protecting groups include silyl groups, for example tri(lower alkyl)silyl groups such as trimethylsilyl; such protecting groups may be introduced by, for example, reactions of the $1\alpha$-hydroxy steroid with the appropriate hexa(lower alkyl)disilazane.

The $1\alpha,3\beta$-dihydroxy steroid-5-enes obtained in accordance with the invention can be converted to the corresponding $1\alpha,3\beta$-dihydroxy steroid-5,7-diene by, for example, conventional techniques such as bromination at the 7-position, e.g. using as brominating agent an N-bromo amide, imide or hydantrin such as N-bromosuccinimide, N-bromophthalimide or dibromodimethylhydantoin, followed by dehydrobromination, e.g. using an amide such as dimethylacetamide in the presence of an alkaline earth metal carbonate. Alternatively dehydrobromination may be induced by treatment with trimethylphosphite or a base such as collidine, pyridine or diazabicyclooctane.

The 7,8-double bond may also be introduced using the method of Daubin et al., e.g. by oxidising the $1\alpha,3\beta$-hydroxysteroid-5-ene to the corresponding steroid-5-en-7-one using a chromium trioxide oxidising agent, advantageously a chromium trioxide/pyridine complex, reacting this ketone with a sulphonyl hydrazine, preferably an aromatic sulphonyl hydrazine such as p-tosyl hydrazine to yield the corresponding 7-sulphonyl hydrazone which is then subjected to Wolff-Kishner reduction conditions, e.g. using an alkali metal alkoxide such as sodium t-butoxide and an alkali metal hydride such as sodium hydride, to yield the desired 5,7-diene.

It may be advantageous to protect the $1\alpha$- and $3\beta$-hydroxy groups, e.g. by esterification to, for example, the dibenzoate, to avoid unwanted side reactions during the reaction sequence required to introduce the 7,8-double bond.

The steroid 5,7-diene resulting from treatment of a compound of formula II by one of the above techniques may be represented by the formula

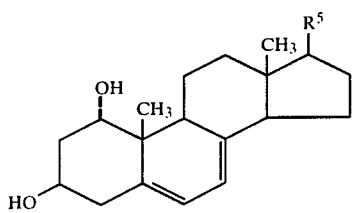

where R⁵ is as defined for formula I.

1α,3β-Dihydroxy-25-hydrogen-cholest-5,7-dienes and hydroxyl-protected derivatives thereof are new compounds.

Irradiation of such a compound of formula III, preferably with near-ultraviolet light e.g. of wavelength 275–300 nm, initially promotes formation of a 1α-hydroxylated previtamin which may be represented by the formula

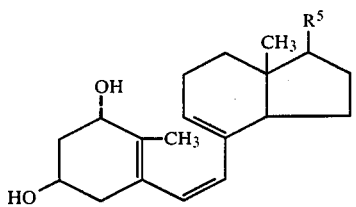

where R⁵ is as defined for formula I. Further irradiation of the compound (IV), or treatment with iodine under mild conditions, e.g. at relatively low temperatures using small quantities of iodine, promotes conversion to the corresponding 1α-hydroxy tachysterol derivative of formula

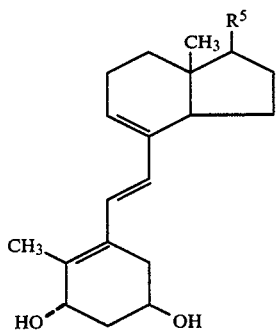

where R⁵ is as defined for formula I, which may, if desired, be reduced, for example with lithium/liquid ammonia or sodium/liquid ammonia to yield a novel 1α-hydroxy-9,10-dihydrotachysterol derivative of potential therapeutic value by virtue of its vitamin D-type activity. 1α-Hydroxy-9,10-dihydrotachysterol itself is a novel compound comprising a feature of the present invention.

The compounds of formula IV also maintain a thermal equilibrium with the vitamin derivatives of formula

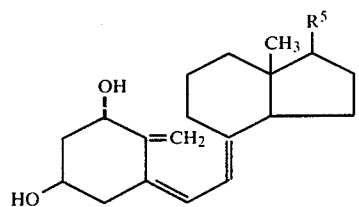

where R⁵ is as defined for formula I, and may be converted into such vitamin derivatives by heating in, for example an alcohol or hydrocarbon solvent. The vitamins have the cis-form shown in formula VI. The formation of unwanted oxidised by products during this conversion may be minimised by esterification of the 1α- and 3β-hydroxy groups, e.g. by conversion to the 1,3-diacetoxy derivative. The vitamin (VI) may if desired by converted to the corresponding 5,6-trans vitamin derivative, isomerisation about the 5,6-double bond readily being promoted by, for example, treatment with iodine under mild conditions.

It will thus be apparent that the 1α,3β-dihydroxy steroid-5-enes prepared in accordance with the present invention are valuable intermediates in the synthesis of a wide range of biologically useful materials.

The starting materials for the reductive process of the invention may be prepared by any convenient method, for example by oxidation of the appropriate 3-hydroxy steroid-5-ene, e.g. using a quinol/quinone oxidising agent such as dichlorodicyanoquinone followed by treatment with a peroxide, e.g. hydrogen peroxide together with a base, e.g. sodium hydroxide, conveniently in an aqueous alcoholic medium to give a 1α,2α-epoxide, which may if desired be converted into the corresponding 1α-hydroxy compound by reduction, e.g. using zinc and an acid such as acetic acid.

The invention also includes as new compounds 1α-hydroxy-25-hydrogen-vitamin D derivatives, especially 1α-hydroxy vitamin $D_2$ and 1α-hydroxy vitamin $D_3$. The invention includes the vitamins (which are in the cis form) and the corresponding trans compounds. The vitamins are superior in vitamin activity not only to vitamin $D_2$ and vitamin $D_3$, but also to the known 1α,25-dihydroxy vitamin D compounds. Thus, for example, the 1α-hydroxy-25-hydrogen compounds exhibit a much more potent effect on bone metabolism; tests in the vitamin $D_3$ series show that 1α-hydroxy-25-hydrogen vitamin $D_3$ is 10–50 times more active than unsubstituted vitamin $D_3$, while 1α,25-dihydroxy vitamin $D_3$ is only 2–5 times more active than the unsubstituted vitamin. These results are particularly surprising in view of previous suggestions that the 25-hydroxy group is involved in metabolism and should therefore be activity promoting. The new 1α-hydroxy-25-hydrogen vitamin D compounds are also quick acting and their biological effect is rapidly terminated, so that the previously encountered problems of vitamin toxicity are substantially avoided by their use.

1α-Hydroxy-25-hydrogen vitamin D compounds, together with 1α-hydroxy-9,10-dihydrotachysterol, thus constitute an important new class of biologically active materials capable of inter alia, stimulating intestinal calcium transport, bone calcium mobilisation, bone mineralisation and bone formation and pharmaceutical compositions containing effective amounts of one or more of these compounds and methods of treatment in human and veterinary medicine involving their administration comprise further features of the present invention.

The said compounds have important prophylactic and therapeutic applications in the prevention or treatment of disorders such as rickets and osteomalacia and are of value in the treatment of vitamin D responsive diseases such as hypoparathyroidism, hypophosphataemia, hypocalcaemia and/or associated bone disease, renal disorders or renal failure and hypocalcaemic tetany. Furthermore, the superior activity of 1α-hydroxy-25-hydrogen vitamin D compounds and 1α-hydroxy-9,10-dihydrotachysterol in comparison with conventional 1-hydrogen vitamin D compounds renders the 1α-hydroxy compounds of value in the treatment of disorders such as vitamin D resistant rickets, renal osteodystrophy, steatorrhea, biliary cirrhosis and other malfunctions of absorption, osteoporosis, secondary hypocalcaemia and/or bone disease arising from dysfunction of the liver, kidneys or gastrointestinal tract, and secondary hypocalcaemia or bone disease resulting from treatment with dilantin, barbiturates such as phenylbarbitone, and related drugs, which prove refractory to conventional compounds such as vitamin $D_3$.

In general 1α-hydroxy-25-hydrogen vitamin D compounds and 1α-hydroxy-9,10-tachysterol may be administered parenterally in combination with an injectable liquid carrier such as sterile pyrogen-free water, sterile peroxide-free ethyl oleate, dehydrated alcohol, propylene glycol or a dehydrated alcohol/propylene glycol mixture. Such compositions may be injected intravenously, intraperitoneally or intramuscularly. Injectable compositions are preferably prepared in dosage unit form, e.g. in ampoules, each unit advantageously containing 0.1–200 μg, preferably containing 0.2–20 μg of the active vitamin ingredient in the case of the vitamin $D_2$ and $D_3$ compounds; the tachysterol compound requires doses in the upper part of the range. The normal dosage for adult human treatment will generally be in the range 0.1–200 μg per day, lower dosages within this range, e.g. 0.1–2 μg being used in prophylaxis and higher dosages, e.g. 5–50 μg being used in therapeutic applications.

In view of the susceptibility of 1α-hydroxy vitamin D compounds and 1α-hydroxy-9,10-dihydrotachysterol to oxidation, we generally prefer that pharmaceutical compositions containing these materials should include at least a trace of an antioxidant such as ascorbic acid, butylated hydroxyanisole or hydroquinone.

We have also found, to our considerable surprise, that the 1α-hydroxy vitamin D compounds and 1α-hydroxy-9,10-dihydrotachysterol exhibit significant activity on oral administration, 1α-hydroxy-vitamin $D_3$ being outstanding in this respect. This is completely unexpected in view of previous disclosures relating to 1α,25-dihydroxy vitamin $D_3$, which have indicated that oral doses of the dihydroxy vitamin have very low activity (e.g. as determined by antirachitic activity measurements) and that parenteral administration of the dihydroxy vitamin is necessary to achieve beneficial therapeutic results; one would normally expect 1α-hydroxy vitamin D compounds to show analogous general behaviour to the corresponding dihydroxy vitamin in view of the similarity in the nature of the biological activity of the compounds in other respects.

The following table, however, which shows the effect on serum calcium and phosphorus levels of parathyroidectomised/thyroidectomised rats (these being male Charles River rats weighing 80–100 g, each test group comprising 6 rats) of oral administration of 1α-hydroxy vitamin $D_3$ (0.1 μg/kg via a gastric intubation), demonstrates that 1α-hydroxy vitamin $D_3$ exhibits good activity on oral administration, as evidenced by the rise in serum calcium level relative to the untreated controls. The table also indicates that the metabolic changes induced by 1α-hydroxy vitamin $D_3$ are of comparatively short duration, the serum calcium level in the 1α-hydroxy vitamin $D_3$-treated rats approaching closely that of the control rats within 24 hours from administration of the vitamin. This confirms that 1α-hydroxy vitamin $D_3$ is rapidly eliminated by the system and so is unlikely to produce undesirable vitamin poisoning side effects.

TABLE I

Effects of orally administered 1α-hydroxy vitamin $D_3$ on serum calcium and phosphorus levels in parathyroidectomised/thyroidectomised rats

| Vitamin administered | Serum calcium level (mg/100 ml) | | Serum phosphorus level (mg/100 ml) | |
|---|---|---|---|---|
| | 8 hrs after administration | 24 hrs after administration | 8 hrs after administration | 24 hrs after administration |
| — (control) | 4.5 ± .43 | 4.8 ± .46 | 12.0 ± .44 | 14.1 ± 1.9 |
| 1α-hydroxy vitamin $D_3$ | 9.9 ± .80 | 6.4 ± .73 | 9.5 ± 1.1 | 14.5 ± 1.0 |

The oral activity and consequent ease of administration of 1α-hydroxy vitamin $D_3$ render this compound of very considerable therapeutic value over a wide range of applications.

The new 1α-hydroxy compounds may, for example, be used as food supplements or components of food supplements, e.g. in combination with other vitamins. One example of such an application is in the fortification of milk, incorporation of 0.1–0.5 μg of 1α-hydroxy vitamin $D_3$ per quart of milk being of value prophylatically in the prevention of disorders such as rickets, osteomalacia etc.

Similarly, the new 1α-hydroxy compounds may be presented in orally administrable pharmaceutical compositions for a wide range of applications, e.g. the treatment of any of the above-mentioned vitamin D responsive or, alternatively any of the 1α-hydroxy vitamin D responsive-conventional vitamin D refractory diseases, particularly the long-term treatment of diseases such as osteoporosis, and prophylactic applications such as vitamin and multi-vitamin preparations.

Orally administrable compositions containing the new 1α-hydroxy compounds may, if desired, contain one or more physiologically compatible carriers and/or excipients and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. The compositions are preferably prepared in dosage unit form, each unit advantageously containing 0.2–20 μg, preferably 0.5–5 μg of 1α-hydroxy compound. The dosage of 1α-hydroxy vitamin $D_3$ employed for adult human treatment with typically be in the range 0.2–20 μg per day. 1α-hydroxy-vitamin $D_2$ is given at similar doses but 1α-hydroxy-9,10-dihydrotachysterol is given at higher doses, e.g. up to 200 μg/day. Tablets and capsules containing the new 1α-hydroxy compounds may, if desired, contain conventional ingredients such as binding agents, for example syrup, acacia, gelatin, sorbitol, tragacanth or polyvinyl-pyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid 1α-hydroxy vitamin $D_3$ compositions may contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats, emulsifying agents, for example lecithin, sorbitan monooleate or acacia; non-aqueous vehicles, which may include edible oils, for example vegetable oils such as arachis oil, almond oil, fractionated coconut oil, fish-liver oils, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

The compositions of the invention may contain other therapeutically useful ingredients such as calcium salts (e.g. the lactate, sodium lactate, phosphate, gluconate or hypophosphite) and/or salts of other essential trace elements such as magnesium, manganese, iron, copper, zinc and iodine and/or other vitamins such as vitamin A, vitamin $B_1$, vitamin $B_2$, nicotinamide, pantothenic acid or salts thereof e.g. the calcium salt, vitamin $B_6$, vitamin $B_{12}$ folic acid, vitamin C and vitamin E. Multivitamin preparations incorporating the new 1α-hydroxy compounds may be formulated in an analogous manner to such vitamin preparations employing conventional 1-hydrogen vitamin D compounds.

The activity of the new 1α-hydroxy compounds also renders the compound suitable for rectal administration, and pharmaceutical compositions for this purpose, e.g. containing an effective dose of 1α-hydroxy vitamin $D_3$ in admixture with a conventional suppository base such as cocoa butter or another glyceride fall within the scope of the invention.

As indicated above, it may be advantageous to incorporate an antioxidant, for example ascorbic acid, butylated hydroxyanisole or hydroquinone in the compositions of the invention to enhance their storage life.

The invention is further illustrated by the following detailed examples. All temperatures are in degrees centigrade.

EXAMPLE 1

(a) Cholesta-1,4,6-trien-3-one

Cholesterol (19.3 gms) and dichlorodicyanoquinone (38 gms) in dry dioxan (500 ml) were heated under reflux for 22 hrs. The mixture was then cooled, filtered and the filtrate evaporated to dryness. Chromatography of the residue on alumina and elution with benzene/hexane followed by elution with benzene afforded the trienone as a pale oil (11.5 gms) which solidified on standing. Physical properties of this material were appropriate.

(b) 1α,2α-epoxycholesta-4,6-dien-3-one

The trienone from (a) (1 gm) in ethanol (50 mls) at 0° was treated with 10% aqueous sodium hydroxide (0.25 ml) and 30% aqueous $H_2O_2$ (2.5 ml). The mixture was stored at 5° overnight and then the resulting epoxide was filtered off, washed with aqueous alcohol and dried to afford the title compound (0.86 mgs). Recrystallization from ethanol gave colourless needles, melting point 107°–109°.

(c) 1α,3β-dihydroxycholest-5-ene

To a stirred solution of lithium metal (0.2 gms) in liquid ammonia (80 ml) and dry tetrahydrofuran (50 mls) containing ammonium chloride (0.5 gms) was added a deoxygenated solution of the epoxide from (b) (4.3 gms) in dry tetrahydrofuran (25 mls) by drops. When the blue colour was discharged the addition of steroid was discontinued and further lithium (0.2 gms) and ammonium chloride (1 gm) were added followed by further addition of the epoxide solution. This sequence was repeated until all of the steroid had been added. At this point an additional piece of lithium (0.2 gms, total 0.8 gms) was added followed by additional ammonium chloride (total 8 gms). Most of the ammonia was then allowed to evaporate and the remaining mixture poured into ice water and extracted with chloroform. Concentration of the chloroform gave a brown gum which was chromatographed on aluminium oxide (160 gms). Elution with ethyl acetate/benzene afforded the 1α,3β-diol as a glass which rapidly crystallized on addition of ethanol. Recrystallization for aqueous ethanol affored the title compound (1.7 gms) melting point 161.5°–163°.

Found: C, 80.40; H, 11.39%: $C_{27}H_{46}O_2$ requires C, 80.54; H, 11.52%.

EXAMPLE 2

(a) 1α-Hydroxycholesta-4,6-diene-3-one

The epoxy dienone from Example 1(b) (130 mgs) in ethanol (10 mls) was treated with zinc dust (1 gm) with stirring followed by addition of 3 drops of acetic acid. The mixture was then filtered and the filtrate concentrated to dryness. Chromatography on silica gel afforded cholesta-1,4,6-trien-3-one (which could be recovered and recycled) followed by the title compound, $\lambda_{max}$ 3600, 3400, 1675, 1625, and 1590 cm$^{-1}$; δ 6.15 (2 protons, s, H6, H7), 5.73 (1 proton singlet H4), δ 4.15 (1 proton, narrow multiplet, H1).

(b) 1α,3β-dihydroxycholest-5-ene

The hydroxy dienone from (a) (0.6 gms) was converted to its trimethylsilyl ether by treatment of a solution in tetrahydrofuran (2 mls) and pyridine (2 mls) with hexamethyldisilazane (1.5 mls) and trimethylchlorosilane (0.6 mls). The crude trimethylsilyl ether was dissolved in tetrahydrofuran (10 mls) and the solution added dropwise to a stirred solution of lithium metal (approx. 200 mgs) in liquid ammonia (20 mls). After a few minutes ammonium chloride (2 gms) was added and the solution stirred. A further portion of lithium metal (approx. 100 mgs) was added. Again the solution was stirred. An additional portion of ammonium chloride was then added and the mixture poured into cold water. The produce was isolated by extraction into ether and methylene dichloride followed by column chromatography which afforded the title compound crystallized from ethanol, melting point 158°–161°. After recrystallisation the melting point was 161.5°–163°. [α]$_D$ (CHCl$_3$)−38°. This material was identical to the product of Example 1(c), and on hydrogenation gave a sample of 1α,3β-dihydroxy-5α-cholestane identical in every way to an authentic specimen.

EXAMPLE 3

(a) 1α,3β-dibenzoyloxycholest-5-ene

1α,3β-dihydroxycholest-5-ene (1.2 gms) was treated in pyridine (10 mls) containing dimethylaminopyridine (20 mgs.) with benzoyl chloride (5 mls). After storage overnight at room temperature, the reaction mixture was poured into water and the product extracted with ether, washed with dilute aqueous hydrochloric acid, saturated bicarbonate solution and water. Evaporation of the ethereal portion gave the dibenzoate (1.6 gms), melting point 147°–150°. Recrystallized from ethanol the product had melting point 151°–153° [α]$_D$+24°.

Analysis:, C$_{41}$H$_{54}$O$_4$ requires C, 80.61%; H, 8.91%: Found: C, 80.43%; H, 8.74%.

(b) 1α,3β-Dibenzoyloxycholesta-5,7-diene

A solution of the dibenzoate described in (a) (0.58 gms) in hexane (10 ml) was treated with dibromodimethylhydantoin (0.15 gms) and heated under reflux for 25 mins. After cooling the mixture was filtered and the filtrate concentrated to a pale oil. The oil was dissolved in dry xylene (3 mls) and added dropwise to a refluxing solution of trimethylphosphite (0.4 ml) in xylene (5 ml.). Heating under reflux continued for 1.75 hrs. after which time the solvents were removed under reduced pressure and the residue crystallized from acetone/methanol to give the title compound. Recrystallized from ethanol/acetone the product had melting point 161°–162°.[α]$_D$−8°.

Analysis: C$_{41}$H$_{52}$O$_4$ requires C, 80.88%; H, 8.61%; Found: C, 80.69%; H, 8.66%.

(c) 1α,3β-Dihydroxycholesta-5,7-diene

The dibenzoate from (b) (300 mgs) dissolved in ethanol (30 mls) and water (0.5 mls) containing KOH (0.6 mgs) was stored at 80° under Argon for 0.5 hrs. The reaction mixture was then cooled and diluted with water and extracted with ether. Evaporation of the ethereal extract gave the tile compound as a crystalline solid. Recrystallization from methanol gave a product with melting point 155°–158°. λ$_{max}$ (ethanol)263 (7,700); 272 (11,000); 282 (11,900); 295 (7,000) nm.

This product (95 mgs.) is deoxygenated ether (200 mls) was irradiated for 12 mins. using a 200 watt Hanovia lamp surrounded by a filtered solution consisting of toluene (24 mls) and CS$_2$ (4 mls) per liter of methanol. The cold solution was transferred into a flask filled with argon and the ether removed at 0°. The residue was dissolved in deoxygenated absolute alcohol (8 mls) and heated under reflux for 1.5 hrs. Biological assay carried out in Vitamin D deficient chicks indicated that the 1α-hydroxy vitamin D$_3$ which was formed (λ$_{max}$. 264 (19,000)) was characterized by the very rapid onset of physiological activity (less than 3 hrs.) which had previously been observed only for the natural product tentatively characterized as 1α,25-dihydroxy Vitamin D$_2$.

EXAMPLE 4

(a) 25-Hydroxycholesta-1,4,6-trien-3-one

25-Hydroxycholesterol (3.4 gms) and dichlorodicyanoquinone (6.5 gms) dissolved in purified dioxan (100 mls) were heated at reflux for 20 hrs. The mixture was filtered and the solvent evaporated. Chromatography of the residue on alumina and elution with ethyl acetate and benzene afforded the trienone. Recrystallization from methanol gave the title compound, melting point 183°–184°. ν$_{max}$. 3600, 1650 and 1600 cm$^{-1}$.

(b) 1α,2α-Epoxy-25-hydroxycholesta-4,6-dien-3-one

The trienone from (a) (1.3 gms) in ethanol (50 mls) was treated with 10% aqueous potassium hydroxide (0.5 ml) and 30% aqueous H$_2$O$_2$ (3 ml). After storage overnight at room temperature, the solution was diluted with water and the solid product collected. Recrystallization from aqueous methanol gave the title compound which after one further crystallization had melting point 162°–163°.

1α,3β-25-Trihydroxycholest-5-ene

The epoxide from (b) was treated with zinc dust and acetic acid as described in Example 2 (a) to yield 1α,25-dihydroxycholesta-4,6-dien-3-one, which was then converted to the trimethylsilyl ether and reduced with lithium/liquid ammonia as described in Example 2 (b). The title compound obtained in this way, (m.p. 171–173 solidifies and remelts at 178°–179°; [α]$_D$−35° in CHCl$_2$) exhibited n.m.r. peaks at δ0.68, 1.02 (methyl groups), δ1.18 (gem-dimethyl groups), δ3.83 (1 proton, narrow signal, 1β-H), δ3.6–4.3 (1 proton, broad signal, 3α-H) and δ5.57 (1-proton, multiplet, 6-H). The 3-monobenzoate thereof melts at 212°–216°; [α]$_D$−20° in CHCl$_3$).

EXAMPLE 5

Irradiation of 1α,3β-diacetoxycholesta-5,7-diene 50 mg of 1α,3β-diacetoxycholesta-5,7-diene (m.p. 118°–119°, prepared by reaction of 1α,3β-dihydroxycholesta-5,7-diene with acetic anhydride using a method similar to that of Example 3 (a)) was irradiated for 11 minutes in deoxygenated ether (200 ml). The UV spectrum of the mixture showed the desired increase in absorption in the region 220–268 nm and a decrease in the region 268–295 nm. It was essentially homogeneous on silica gel (CHCl$_3$) but separated into two clean spots on 1% AgNO$_3$-silica gel-chloroform, the lower spot corresponding to starting material in R$_f$. The less polar matrial (approx. 20 mg) had a broad UV absorption band with a "flat" max. around 262–272 nm (small hump at 282 and 295 nm) and a min. at 234 nm. This material comprised crude previtamin. A small amount of this mixture was dissolved in hexane and the UV recorded (est. conc. approx. 20 mg per liter). This was then treated with a solution of iodine in hexane so that the overall concentration of iodine was approximately 0.4 mg. per liter and kept in diffuse light for 45 min. The hexane solution was washed with dilute aqueous sodium thiosulphate, then water, dried and the UV spectrum re-recorded. This showed absorptions characteristic of a tachysterol derivative (max. at 282 nm and shoulders at 272, 292 nm) and the absorbance had increased by a factor of 2.2.

The bulk of the crude previtamin was dissolved in deoxygenated iso-octane (10 ml). The absorbance at 262 nm was 0.39 when a 30 μl aliquot was diluted to 3 ml. The solution was then heated at approximately 75°, under argon, for a total of 2.25 hrs. during which time the absorbance at 262–265 nm increased to a max. of 0.54 (for a solution of the same concentration as above). As expected, the absorbance increased rapidly at first and then slowly as the equilibrium mixture was approached. Treatment of an aliquot with iodine in hexane as above revealed absorptions characteristic of tachysterol but the increase in absorbance was only from 0.43 to 0.47. The equilibrated mixture was essentially homogeneous on both silica gel and 1% $AgNO_3$-silica gel (developed in chloroform).

Approx. 12 mg. of the mixture was dissolved in deoxygenated methanol (1.0 ml), the solution treated with deoxygenated 1.5% methanolic KOH (0.5 ml) and kept under argon at room temperature for 1.5 hrs. Dilution with water and ether extraction gave the $1\alpha,3\beta$-diols which showed as two very close major spots on silica gel (developed with 4% MeOH—$CHCl_3$). The less polar fraction (approx. 5 mg) exhibited a broad absorption in the UV with a max. at 264 nm and a min. at 228 nm. This was $1\alpha$-hydroxy vitamin $D_3$. Treatment of an aliquot with iodine in hexane, as above, produced a shift in the max. to 270 nm, this resulting from conversion into 5,6-trans vitamin.

The more polar fraction had a smooth absorption band in the UV with max. at 260 nm and min. at 235 nm. This was the previtamin. Treatment of this with iodine, as above, gave a complex UV spectrum with maxima at 268, 276, 286, 298, 312 and 327 nm.

EXAMPLE 6

1α-Hydroxy vitamin D₃

Irradiation of 135 mg. of $1\alpha,3\beta$-diacetoxycholesta-5,7-diene (prepared as in Example 5) in deoxygenated ether (200 ml) for 15 minutes and separation of the products on 1% $AgNO_3$-silica gel ($CHCl_3$) (preparative t.l.c.) gave 68 mg. starting material (more polar fraction) and the crude previtamin (54 mg, less polar fraction).

The previtamin so obtained was heated at 75° for 2 hours in deoxygenated iso-octane (15 ml) under argon.

The resulting mixture of vitamin and previtamin was dissolved in methanol (4 ml) and the solution treated with 1 ml 2.5% methanolic KOH and kept at room temperature for 2 hours. Dilution with water and extraction with ether gave the vitamin and previtamin diols, which were separated on silica gel (preparative t.l.c.) (8% MeOH—$CHCl_3$) to give 13 mg of the vitamin ($R_f$ 0.35) and 8 mg of the previtamin ($R_f$ 0.31). Recrystallisation of the vitamin from ether-pentane gave fine colorless needles m.p. 132°–133° (rate of heating 1°/4 sec.), m.p. 128°–129° (rate of heating 1°/25 sec.). UV (ether) $\lambda_{max}$ 264 nm (20,200), $\lambda_{min}$ 229 nm (10.800). There is 9% uncertainty in extinction values but the ratio (λ max)/(λ min) is 1.87±10%. $[\alpha]_D^{20°}$ (ether: C~0.3%)+26°±2°. Product $[\alpha]_D^{20°}$ ×extinction at 264 nm ~5.2×10⁵±10%. $\nu_{max}$. ($CHCl_3$) 3700, 3500, 1600–1650, 1040 cm⁻¹. NMR (d₆ acetone) $H_6+H_7$ AB quartet at δ6.20 (apparent J=11.5 Hz). $H_{19}$ two narrow one-proton multiplets at δ4.92 and δ5.37 ppm. The previtamin ($\lambda_{max}$ 260 nm and $\lambda_{min}$ 232 nm) (11 mg from two separate irradiations) was dissolved in deoxygenated iso-octane (8 ml) and heated at 75° for 1.5 hours. Isolation by preparative t.l.c. as before gave a further 4.6 mg of the vitamin. Decomposition occurred here and practically no previtamin remained.

Analysis for 1α-hydroxy vitamin $D_3$: Found C 80.6%, H 11.04%, $C_{27}H_{44}O_2$ requires C 80.9%, H 11.07%

EXAMPLE 7

(a) The cholest-5-ene from Example 4 (c) was acetylated with acetic anhydride/pyridine to yield the triacetate which was subjected to bromination with dibromodimethylhydantoin followed by dehydrobromination with trimethylphosphite according to the procedure of Example 3 (b) to yield, after chromatography on silver nitrate impregnated silica gel, $1\alpha,3\beta,25$-triacetoxycholesta-5,7-diene (m.p. 96°–101°; $\alpha_D$−24° in $CHCl_3$; $\lambda_{max}^{Et2O}$ 262 (7,900), 271 (11,500), 282 (12,400), 294 (7,300) nm.

(b) The cholesta-5,7-diene from (a) above was irradiated by the procedure of Example 6, using a medium pressure mercury lamp, to yield a mixture of isomers from which unchanged cholesta-5,7-diene was recovered by chromatography on silver nitrate impregnated silica gel. The balance of the irradiation product, which comprised largely the previtamin triacetate [based on the iodine catalyzed transformation of the previtamin into the tachysterol analogue ($\lambda_{max}$.260→$\lambda_{max}$.272, 282, 292 nm; 100% purity requires a 3-fold increase in absorbance, found 1.9)] was heated at 70° for 2 hrs. in deoxygenated isooctane under argon to effect equilibration of the previtamin and vitamin triacetates. Saponification (5% KOH in methanol) led to a mixture of previtamin and vitamin triols from which the desired vitamin was isolated by preparative thin layer chromatography. 1α,25-Dihydroxy-vitamin $D_3$, crystallised by precipitation from ether with hexane, had m.p. 84°–88°; $[\alpha]_D+29°$ (in Et₂O); $\lambda_{max}^{Et2O}$ 264 (18,000), $\lambda_{min}$. 228.5 (10,100) nm; ¹H NMR: 0.57 (3H, s, $C_{18}$ ($H_3$)), 1.13 (6H, s, $C_{26}$, $C_{27}$ ($H_3$)), 4.85, 5.30 (2H, double narrow multiplet $C_{19}$ ($H_2$)), 6.20 (2H, AB quartet, J=11.5 Hz $C_6$, $C_7$ ($H_2$)) δ; analysis: (Found: C, 77.84; H, 10.53; $C_{27}H_{44}O_3$ requires: C, 77.83; H, 10.65). Crystallised from $CHCl_3$, 1α,25-dihydroxy vitamin $D_3$ was obtained as the monochloroform solvate, m.p. 106°–112°; $\lambda_{max}^{Et2O}$ 264 (18,000), $\lambda_{min}$. 228.5 (9,900) nm; m/e 416.3291 ($C_{27}H_{44}O_3$ requires 416.3290); analysis: (Found: C, 62.19; H, 8.48; $C_{27}H_{44}O_3$·$CHCl_3$ requires: C, 62.74; H, 8.46). On treatment with $I_2$ the 1α,25-dihydroxy vitamin $D_3$ underwent a smooth transformation accompanied by spectral changes analogous to those accompanying the transformation of 1α-hydroxy vitamin $C_3$ into the corresponding 5,6-trans-isomer.

EXAMPLE 8

Orally administrable 1-hydroxy vitamin D₃ compositions (a) 1α-hydroxy vitamin $D_3$ capsules 1α-hydroxy vitamin $D_3$ is dissolved in sterile arachis oil of low peroxide containing 0.1° w/w butylated hydroxyanisole as antioxidant to give a solution with a vitamin concentration of 40 μg/ml. ¼ ml portions of the resulting solution are encapsulated in gelatin by conventional techniques.

Dose-1-2 capsules per day.

Capsules were also prepared by the above method from solutions containing 2.0 μg/ml and 4.0 μg/ml respectively of 1α-hydroxy vitamin $D_3$.

(b) Tri-vitamin preparation

Tablets comprising the following ingredients are prepared by conventional techniques:

| Vitamin A | 4000 u.s.p. units |
|---|---|
| Vitamin C | 75 mg |
| 1α-Hydroxy vitamin $D_3$ | 0.2–1 μg |

The preparation may optionally also contain 1 mg. of fluorine as a phsiologically compatible fluoride salt.
Dose-1 tablet per day.

(c) Deca-vitamin preparation (for adult use)

Tablets comprising the following ingredients are prepared by conventional techniques:

| Vitamin A | 25,000 u.s.p. units |
|---|---|
| Vitamin $B_1$ | 10 mg |
| Vitamin $B_2$ | 10 mg |
| Vitamin $B_6$ | 5 mg |
| Vitamin $B_{12}$ | 5 μg |
| Vitamin C | 200 mg |
| 1α-Hydroxy vitamin $D_3$ | 0.2–1 μg |
| Vitamin E | 15 I.U. |
| Calcium pantotienate | 20 mg |
| Nicotinamide | 100 mg |

The tablets may optionally also contain 1 mg of fluorine as a physiologically compatible fluoride salt and/or a mineral complex comprising the following elements in the form of physiologically compatible salts:

| Copper | 2 mg |
|---|---|
| Iodine | 0.15 mg |
| Iron | 12 mg |
| Magnesium | 65 mg |
| Manganese | 1 mg |
| Zinc | 1.5 mg |

Dose-1 tablet per day.

(d) Deca-vitamin preparation (for infants and children)

Tablets comprising the following ingredients are prepared by conventional techniques:

| Vitamin A | 5000 u.s.p. units |
|---|---|
| Vitamin $B_1$ | 5 mg |
| Vitamin $B_2$ | 5 mg |
| Vitamin $B_6$ | 2 mg |
| Vitamin $B_{12}$ | 10 μg |
| Vitamin C | 100 mg |
| 1α-Hydroxy vitamin $D_3$ | 0.2–1 μg |
| Calcium pantothenate | 3 mg |
| Nicotinamide | 30 mg |

The tablets may optionally also contain a phsiologically compatible fluoride salt or mineral complex in the quantities set out in (c) above.
Dose-1 tablet per day.

(e) Feed Composition For Poultry 40 micrograms of 1α-hydroxy vitamin $D_3$ are dissolved in ethanol (100–500 ml) and the resulting solution is slurried with 2 kg of ground limestone. The ethanol is then removed under reduced pressure, with stirring of the slurry, and the resulting vitamin-containing solid is added to poultry feed at a rate of 20 grams per kg of feed.

EXAMPLE 9

(a) 1α,2α-Epoxy-25-hydroxycholesta-4,6-diene-3-one

The trienone from Example 4(a) (5.4 g) in ethanol (250 ml) was treated with 50% hydrogen peroxide (5 ml) and 10% aq. KOH (1 ml) and the solution kept at 5° for 16 hours (reaction not complete). The solution was treated with further portions of 50% hydrogen peroxide (5 ml) and 10% KOH (1 ml) and stirred at room temperature for 7 hours (reactions followed by thin layer chromatography (t.l.c.). The solution was diluted with water, the product collected and recrystallized from aqueous ethanol to give colourless needles of the title compound (4.1 g, 73%) m.p. 160°–162°.

(b) 1α,25-Dihydroxycholesterol

Lithium metal (0.65 g) was dissolved in liquid ammonia (100 ml) and to this was added purified tetrahydrofuran (THF) (80 ml). The epoxy-dienone of (a) above (1.24 g, 3 m. moles) in THF (20 ml) and solid $NH_4Cl$ (9 g) were added slowly (5–10 min.) and simultaneously to the stirred lithium solution. The mixture was stirred until the blue colour was discharged (5–10 min.) and then a further piece (0.1 g) of lithium metal was added to ensure complete reduction. When the solution was again colourless, the ammonia was allowed to evaporated, the remaining mixture was diluted with water and extracted with chloroform. Evaporation of the chloroform gave a colourless gum which was chromatographed on alumina (act. IV, 50 g) (compound introduced onto the column adsorbed on alumina 1V, 10 g). Elution with benzene-ethyl acetate (3:2) gave the less polar contaminants followed by the title compound as a colourless solid (0.76 g, 60%). (Small amounts of impure title compound eluted with early and late fractions was not recovered, i.e. the yield is actually better than 60%).

Recrystallization from acetone-acetonitrile gave colourless needles of (0.71 g) as the hemiacetonate. The acetone of crystallization was observed in the NMR at δ1.97 (pyridine as solvent) and in the IR at 1710 cm$^{-1}$. The acetone was bound strongly and it was removed completely only after heating at 80°/0.2 mm for 2 days. The melting point of this material varied with the rate of heating. On slow heating above 160° it melted at 171°–173° followed by slow but complete resolidification (temp. held around 173° for a couple of minutes) and remelted at 177°–179°. $[\alpha]_D - 35°$ (CHCl$_3$) Found: C, 77.46; H, 10.98; $C_{27}H_{46}O_3$ requires C, 77.46; H, 11.08. $\nu_{max.}$ (nujol) 3400, 1050 cm$^{-1}$. δ(CDCl$_3$) 5.60 (1 proton, narrow multiplet, H$_6$), δ3.86 (2 protons, one narrow and one broad multiplet, H$_1$ and H$_3$), δ1.20 (strong singlet, C$_{26}$ and C$_{27}$ methyls), δ1.02 and 0.67 (singlets C$_{19}$ and C$_{18}$ methyls). Reduction of 2.3 g of epoxide (IV) by doubling all the reagents gave 1.32 g of triol (V).

(c) 1α,25-Dihydroxycholesterol-3-benzoate

To a solution of the triol from (b) above (80 mg) in pyridine (0.8 ml) was added benzoic anhydride (0.65 g) and the solution was kept at room temperature. After several days the reaction mixture consisted of mostly monobenzoate, a small amount of dibenzoate and a trace of the starting triol. Separation of the mixture by prep. tl.lc. (silica gel, 3% MeOH—CHCl$_3$) gave the title monobenzoate (64 mg) as a colourless crystalline solid. Recrystallization from ethanol yielded colourless prisms (55 mg) m.p. 212°–216° (unchanged on further recrystallization. $[\alpha]_D-20°$ (CHCl$_3$). Found: C, 77.87; H, 9.42. C$_{34}$H$_{50}$O$_4$ requires: C, 78.12; H, 9.64. $\nu_{max}$. (nujol) 3550, 1700 cm$^{-1}$. (CDCl$_3$): 8.3–7.4 (5 protons, multiplets, aromatic protons), 5.70 (1 proton, narrow multiplet, H$_6$), δ5.3 (1 proton, broad multiplet, H$_3$), δ3.95 (1 proton, narrow multiplet, H$_1$), δ1.21, 1.07, 0.68 (singlets, C$_{26-27}$, C$_{18}$ methyls respectively).

The 1.3-dibenzoate of the triol (10 mg) was also obtained by preparative t.l.c. Its NMR spectrum showed the aromatic protons between δ8.3–7.3, H$_6$ was a narrow multiplet at 5.7, H$_1$ and H$_3$ gave rise to one narrow and one broad multiplet at δ5.4, the C$_{26}$, C$_{27}$ and C$_{19}$ methyls produced a singlet at δ1.20 and the C$_{18}$ methyl was a singlet at δ0.67.

(d) Hydrolysis of Monobenzoate

The monobenzoate from (c) above (10 mg) was dissolved in boiling ethanol (5 ml), the solution cooled, treated with KOH (100 mg) in water (few drops) and kept overnight at room temperature. It was then neutralized with acetic acid, the solvents removed at reduced pressure and the residue extracted with chloroform and washed with water. Evaporation of the chloroform gave a solid which on recrystallization from acetone-acetonitrile afforded colourless needles of the triol m.p. 171°–173° and 177°–179°, identical to that described above.

(e) 1α,25-Dihydroxycholesterol-tris-trimethylsilyl ether

The tris-trimethylsilyl ether was prepared by treatment of a solution of the triol from (b) above (2 mg) in pyridine (0.2 ml) with TBT (0.2 ml) at room temperature for 1 hour. [TBT is trimethylsily imidazole+trimethylsilyl acetamide+trimethylchlorosilane (3:3:2)]. G.l.c. analysis on a 6′, 3% QFI column at 212° revealed a single peak with retention time of 5.6 minutes.

(f) 1α,25-Dihydroxycholesterol-triacetate

The triol from (b) above (0.5 g) in pyridine (0.5 ml) and acetic anhydride (8 ml) was heated at reflux for 1.5 hours. The solution was cooled, poured into ice-water and stirred to decompose the anhydride. Work up by extraction with ethyl acetate as usual gave a brown oil which was chromatographed on alumina (act. III, 25 g). Elution with hexane-benzene (7:3) gave a trace of non polar material. Benzene-hexane (1:1) yielded the title compound (0.58 g) as a very soluble colourless oil which resisted all attempts at crystallization. This material was homogeneous on t.l.c. on silica gel, alumina and silica gel-silver nitrate. $\nu_{max}$. (film) 1730 cm$^{-1}$ (CDCl$_3$) 5.50 (1 proton, narrow multiplet, H$_6$), δ5.2–4.6 (2 protons, one broad and one narrow multiplet, H$_1$ and H$_3$ with H$_1$ as a narrow multiplet at δ5.03), 2.00, 1.98, 1.91 (singlets, acetates), 1.40, 1.05, 0.67 (singlets, C$_{26-27}$, C$_{19}$, C$_{18}$ methyls respectively.

(g) 1α,3β,25-Triacetoxy-cholesta-5,7-dione

The above ene-triacetate from (f) above (0.58 g) in hexane (10 ml) was treated with dibromodimethylhydantoin (170 mg, 1.1 equiv.). The mixture was heated at reflux for 15 min, cooled, filtered and the solvent evaporated to give a pale brown oil. This, in xylene (5 ml) was added to a refluxing solution of trimethylphosphite (0.6 ml) in xylene (5 ml.). The solution was heated at reflux for 1.5 hours and the solvents evaporated at reduced pressure (oil pump). Attempts to resolve the mixture by chromatography on a 30 inch column packed with 2% AgNO$_3$-silica gel (ratio of adsorbent to mixture, 250:1) failed to give any pure 5,7-diene. Preparative t.l.c. on silica gel-AgNO$_3$ (10, 200×200×1 mm plates, prepared by dipping commercial plates in a 2% AgNO$_3$ solution in acetonitrile and drying at 150° F. with air slow for 1.5 hours.) gave the title 5,7-diend (175 mg, 30%) as the more polar band visible under the UV upon development of the plates twice in 0.4% MeOH—CHCl$_3$. Crystallization from aqueous methanol yielded fine colourless needles m.p. 96°–101° unchanged on further recrystallization. $[\alpha]_D-24°$(CHCl$_3$). Found: C, 72.84; H, 9.16 C$_{33}$H$_{50}$O$_6$ requires: C, 73.03; H, 9.29. $\nu_{max}$. (nujol) 1735 cm$^{-1}$. at 272 and 292 nm) and an increase in absorbance by a factor of approx. 1.9.

The crude previtamin was heated at 75° for 2 hours in deoxygenated isooctane (20 ml) during which time the absorbance at 260–265 nm increased by 20–25% (isomerization to the vitamin). At this point the mixture was still essentially homogeneous on t.l.c. and the UV peaks at 274, 285 and 298 nm remained.

The iso-octane was removed at reduced pressure and the resulting pale brown oil was subjected to hydrolysis in deoxygenated 3% methanolic KOH (10 ml) at room temperature for 16 hours. The mixture was worked up by dilution with water and extracted with ether to give a brown oil. Attempts to resolve the mixture on 8, 200×200×1 mm silica gel plates (developed 2x's with 6% MeOH—CHCl$_3$) afforded three major fractions of R$_f$ approx. 0.2, 0.4 and 0.6 in the ratio of approx. 2:2:1. The most polar band (which was almost separated into two bands) contained a mixture of the previtamin and title vitamin and showed a single clean UV absorption with max. at 263 and min. at 227 nm.

The intermediate fraction had UV max. at 273, 285 and 298 nm but also showed considerable absorption in the 220–260 nm region and may have contained some partially acetylated vitamin and previtamin. The IR of this fraction showed weak carbonyls at 1720 and 1740 cm$^{-1}$. Further hydrolysis as above produced an additional 2 mg of the title vitamin.

The least polar fractions showed UV peaks at 275, 286 and 299 nm with practically no absorption in the 220–260 nm region and therefore did not contain any of the desired vitamin or previtamin.

The vitamin-previtamin mixture (fraction I above) was rechromatographed on 10, 200×200×1 mm silica gel plates, developing 2x's with 5% MeOH—CHCl$_3$. This gave rise to two thin bands separated by approx. 1 mm. Careful isolation and extraction with 8% MeOH-ether followed by washing with water, drying and evaporating gave the title vitamin (12.5 mg, 18% conversion) (less polar band) as a colourless gum. Attempts to crystallize it by dissolving in a min. amount of ether and diluting with pentane to incipient cloudiness and refrigerating resulted in an oil. Aqueous methanol had the same end result.

The title vitamin was obtained as a colourless powder by swamping an ether solution with pentane. This had m.p. 84°–88° and $[\alpha]_D+29°$ (CHCl$_3$). Found: C, 77.84; H, 10.53. C$_{27}$H$_{44}$O$_3$ requires: C, 77.83; H, 10.65. $\nu_{max}$. 264 (18000), $\lambda_{min}$. 228.5 nm (10100). $\nu_{max}$. (CHCl$_3$) 3650 (sharp), 3500 (broad) 1600–1650 cm$^{-1}$. (NMR in D$_6$ Acetone 6.20 (2 proton, AB quartet, J=11.5 Hz, H$_6$ and H$_7$), 5.30 and 4.85 (1 proton each, narrow multiplets, 2H$_{19}$), 1.13 and 0.57 (sharp singlets. C$_{26-27}$ and C$_{18}$ methyls respectively). The mass spectrum showed M+ at 416 followed by alternate loss of H₂O and CH₃, 3x's (398, 383, 380, 365, 362, 347) and the fragments at m/e 287 (loss of side chain due to cleavage between $C_{17}$ and $C_{20}$) and m/e 152 (cleavage between $C_7$ and $C_8$).

During the running of the IR in chloroform, it was noticed that the title vitamin began to crystallize. Therefore, it was dissolved in a min. of chloroform and in a few minutes. it was precipitated almost quantitatively as colourless prisms, m.p. 106°-112°. Found: C, 62.19; H, 8.48. $C_{27}H_{44}O_3.CHCl_3$ requires: C, 62.74; H, 8.46. $\lambda_{max}$. 264 (18,000), $\lambda_{min}$. 228.5 nm (9900), calculated for $C_{27}H_{44}O_3.CHCl_3$.

The mass spectrum showed M+ at 416.3291 (required for $C_{27}H_{44}O_3$, 416.3290) and also a pattern at m/e 83/85 attributed to the CHCl₃ of crystallization.

The more polar band from the prep. plates above gave the previtamin (5.5 mg, 8% conversion) $\lambda_{max}$. 260 nm which showed a hump at approximately 250 nm. Further vitamin could be obtained by heating the previtamin in iso-octane (vide supra).

EXAMPLE 10

1α,3β-Diacetoxycholesta-5,7-diene

1αOH cholesterol diacetate (0.25 gms) in hexane (10 ml) containing dimethyl dibromo hydantoin (0.2 gms) was heated under reflux for 15 minutes cooled, filtered, and the filtrate concentrated to give a pale yellow oil which was dissolved in xylene (4 mls) and added dropwise to a solution of trimethylphosphite (6 mls) in xylene (5 mls) maintained at reflux. Heating was continued for 1.5 hours under argon. The mixture was the concentrated under reduced pressure and the produce separated on silver nitrate impregnated silica gel plates. Crystallization from methanol gave 130 mgs. (34%) melting point 118°-119° $[\alpha]_D$ (CHCl₃): −31°.

Analysis: Found: C 76.75 H, 9.99 $C_{31}H_{48}O_4$ requires C 76.81 H 9.98 $\lambda_{max}$. (ether) 262 (8,300); 271 (11,800); 282 (12,700); 294 nm (7,500). NMR: 4.97 (narrow multiplet, H₁), 4.6–5.2 (broad, multiplet H₃), 5.2–5.75 (double doublets further coupled H₆ and H₇), 2.02 and 2.07 (singlets, acetates).

Direct acetylation of the diene diol described in the specification gave diacetate with the same physical characteristics.

We claim:

1. A process for the preparation of a 1α-hydroxyvitamin D compound wherein a compound of the formula:

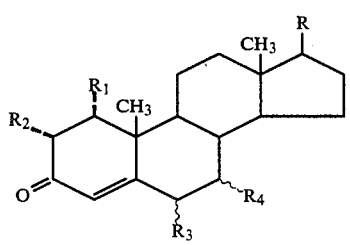

in which R is a group of the formula:

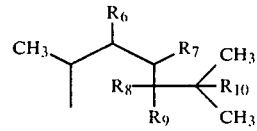

wherein R₆ and R₇ are each H or —OH or together form a carbon-carbon bond or epoxy group, R₈ and R₁₀ are each —H or —OH and R₉ is H, —CH₃ or —C₂H₅; R₁ is OH or protected OH and R₂ is H or R₁ and R₂ together represent an epoxide group; R₃ represents a reductively eliminatable atom or group and R₄ is H or R₃ and R₄ together represent a carbon-carbon bond, is treated with a reagent selected from the group consisting of an alkali metal/liquid ammonia and an alkali metal/amine reducing agent in the presence of a proton source, to form the corresponding 1α,3β-dihydroxy-5-ene of the formula:

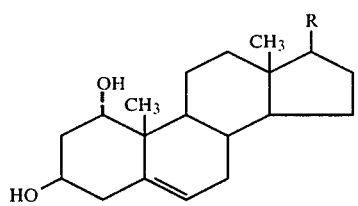

where R has the above meaning, then introducing a 7,8-double bond to form the corresponding 5,7-diene of the formula:

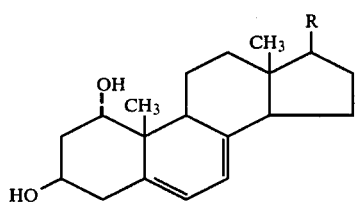

said 5,7-diene then being irradiated to form a previtamin of the formula:

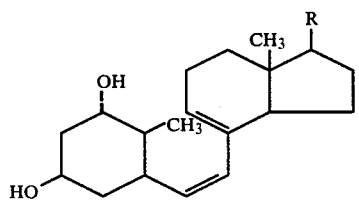

which is then isomerised to give the desired 1α-hydroxy vitamin D compound.

2. A process for the preparation of 1α-hydroxy-25-vitamin D or acylates thereof in which 1α-hydroxy-25-hydrogen-previtamin D or an acylate thereof is isomerised by heating to yield the desired vitamin D compound, wherein the cis-1α-hydroxy-25-hydrogen is treated with iodine to effect isomerisation to the corresponding trans isomer.

* * * * *